(12) United States Patent
Stergiou et al.

(10) Patent No.: US 9,179,862 B2
(45) Date of Patent: Nov. 10, 2015

(54) METHOD AND SYSTEM FOR ASSESSING LOCOMOTIVE BIO-RHYTHMS

(75) Inventors: Nikolaos Stergiou, Omaha, NE (US); Maximilian Joseph Kurz, Omaha, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 1830 days.

(21) Appl. No.: 11/184,490

(22) Filed: Jul. 19, 2005

(65) Prior Publication Data

US 2007/0021689 A1    Jan. 25, 2007

(51) Int. Cl.
*A61B 5/103* (2006.01)
*A61B 5/00* (2006.01)

(52) U.S. Cl.
CPC ............. *A61B 5/1038* (2013.01); *A61B 5/7264* (2013.01); *A61B 5/7282* (2013.01)

(58) Field of Classification Search
CPC .... A61B 5/1036; A61B 5/1118; A61B 5/112; A61B 5/1133
USPC .............. 600/595, 546, 300, 558, 559; 706/8; 377/24; 601/5
See application file for complete search history.

(56) References Cited

U.S. PATENT DOCUMENTS

| | | | |
|---|---|---|---|
| 4,647,918 A * | 3/1987 | Goforth ...................... 340/573.1 |
| 4,745,930 A * | 5/1988 | Confer ........................... 600/592 |
| 4,813,436 A * | 3/1989 | Au ................................ 600/592 |
| 5,280,265 A * | 1/1994 | Kramer et al. ................. 338/210 |
| 5,511,561 A * | 4/1996 | Wanderman et al. .......... 600/592 |
| 5,619,186 A * | 4/1997 | Schmidt et al. ............. 340/573.1 |
| 6,174,294 B1 * | 1/2001 | Crabb et al. ................... 600/592 |
| 6,183,425 B1 * | 2/2001 | Whalen et al. ................ 600/592 |
| 6,231,527 B1 * | 5/2001 | Sol ................................ 600/595 |
| 6,360,597 B1 | 3/2002 | Hubbard, Jr. |
| 6,473,483 B2 * | 10/2002 | Pyles ............................... 377/24 |
| 6,522,266 B1 * | 2/2003 | Soehren et al. ............... 340/988 |
| 6,836,744 B1 | 12/2004 | Asphahani et al. |
| 7,355,519 B2 * | 4/2008 | Grold et al. ................. 340/573.7 |
| 8,308,665 B2 * | 11/2012 | Harry et al. ...................... 601/22 |
| 8,974,402 B2 * | 3/2015 | Oddsson et al. .............. 600/595 |
| 2002/0077534 A1 * | 6/2002 | DuRousseau ................. 600/300 |

(Continued)

OTHER PUBLICATIONS

Ross Bogey et al., Computer Algorithms to Characterize Individual Subject EMG Profiles During Gait, Arch Phys Med Rehabil, Sep. 1992, pp. 835-841, vol. 73.

(Continued)

*Primary Examiner* — Sean Dougherty
(74) *Attorney, Agent, or Firm* — Marshall, Gerstein & Borun LLP

(57) ABSTRACT

A method, system, and article of manufacture for detecting, recording, quantifying, and classifying gait data. In one embodiment, the method of the invention includes a step of detecting foot contact events using a portable sensor device. Stride data is collected by processing the detected foot contact events to obtain and record gait pattern data. At least one gait stability value is determined from the gait pattern data using a specified gait stability metric. The gait stability value is preferably a mathematical chaos value which is processed utilizing clustering correlation to classify the gait pattern data in association with a neuromuscular status. In a preferred embodiment, fuzzy logic is utilized to correlate the determined gait stability value with a plurality of gait stability values each associated with a distinct neuromuscular status.

20 Claims, 5 Drawing Sheets

(56) References Cited

U.S. PATENT DOCUMENTS

| | | | | |
|---|---|---|---|---|
| 2004/0143170 | A1* | 7/2004 | DuRousseau | 600/300 |
| 2004/0249319 | A1* | 12/2004 | Dariush | 601/5 |
| 2005/0004495 | A1* | 1/2005 | Goswami | 600/595 |
| 2005/0010139 | A1* | 1/2005 | Aminian et al. | 600/595 |
| 2005/0033200 | A1* | 2/2005 | Soehren et al. | 600/595 |
| 2005/0240086 | A1* | 10/2005 | Akay | 600/300 |
| 2006/0015470 | A1* | 1/2006 | Lauer et al. | 706/8 |
| 2006/0056655 | A1* | 3/2006 | Wen et al. | 382/103 |
| 2006/0100546 | A1* | 5/2006 | Silk | 600/592 |
| 2007/0203435 | A1* | 8/2007 | Novak | 601/70 |

OTHER PUBLICATIONS

Ugo Buzzi, An Investigation Into the Dynamics of Parkinsonian Gait, A Thesis Presented to the School of Health, Physical Education, and Recreation, and the Faculty of the Graduate College University of Nebraska at Omaha, Jul. 2001.

Ugo Buzzi et al., Nonlinear Dynamics Indicates Aging Affects Variability During Gait, Clinical Biomechanics, 2003, pp. 435-443, vol. 18.

J. Dingwell et al., Local Dynamic Stability Versus Kinetic Variability of Continuous Overground and Treadmill Walking, Journal of Biomechanical Engineering, Feb. 2001, pp. 27-32, vol. 123.

J. Dingwell et al., Slower Speeds in Patients With Diabetic Neuropathy Lead to Improved Local Dynamic Stability of Continuous Overground Walking, Journal of Biomechanics, 2000, pp. 1269-1277, vol. 33.

Ary Goldberger et al., Fractal Dynamics in Physiology: Alterations With Disease and Aging, PNAS, Feb. 19, 2002, pp. 2466-2472, vol. 99, Suppl. 1.

Jeffrey Hausdorff et al., Altered Fractal Dynamics of Gait: Reduced Stride-Interval Correlations With Aging and Huntington's Disease, The American Physiological Society, 1997, pp. 262-269.

Jeffrey Hausdorff et al., Dynamic Markers of Altered Gait Rhythm in Amyotrophic Lateral Sclerosis, Journal of Applied Physiology, 2000, pp. 2045-2053, vol. 88.

Jeffrey Hausdorff et al., Fractal Dynamics of Human Gait: Stability of Long-Range Correlations in Stride Interval Fluctuations, The American Physiological Society, 1996, pp. 1448-1457.

Jeffrey Hausdorff et al., Footswitch System for Measurement of the Temporal Parameters of Gait, Journal of Biomechanics, 1995, pp. 347-351, vol. 28, No. 3.

Jeffrey Hausdorff et al., Is Walking a Random Walk? Evidence for Long-Range Correlations in Stride Interval of Human Gait, The American Physiological Society, 1995, pp. 349-358.

Jeffrey Hausdorff et al., Maturation of Gait Dynamics: Stride-to-Stride Variability and its Temporal Organization in Children, The American Physiological Society, 1999, pp. 1040-1047.

Max Kurz et al., Controlling Bifurcations and Chaotic Gait With Hip Joint Actuations in a Simple Walking Model, Proceedings of the American Society of Biomechanics Annual Meeting, Toledo, 2003.

Manabu Miyamoto et al., A Novel Device for Measuring Fluctuations in Stride Intervals of Human Gait, Bulletin of the Osaka Medical College, 2002, pp. 19-25, vol. 48.

* cited by examiner

METHOD AND SYSTEM FOR ASSESSING LOCOMOTIVE BIO-RHYTHMS

BACKGROUND OF THE INVENTION

1. Technical Field

The present invention relates generally to processing locomotive biometrics, and in particular to determining, quantifying, and classifying gait patterns. More particularly, the present invention relates to a method, apparatus, system, and article of manufacture for detecting and processing gait pattern data in a manner enabling correlation with neuromuscular conditions associated therewith.

2. Description of the Related Art

Auto-locomotion in humans and animals is a complex neuromuscular activity. The dynamic characteristics of such locomotion are often referred to as gait. Temporal and distance factors of gait are often referred to as stride characteristics. Given the dependence of gait characteristics on a multitude of neuromuscular factors, the study of gait, particularly the variability of stride and/or other gait-related metrics, may be very useful for medical diagnostic and prognostic purposes.

Conventional systems and techniques for analyzing gait include clinician observation, kinematics methods, and kinetic methods. Extensive training and experience are required for a clinician to accurately assess subject's gait pattern and correlate such observations with underlying neuromuscular conditions. Even with extensive training and experience, clinician observation of gait is considerably imprecise, particularly for evaluating subtle gait characteristics that may be useful in detecting slight changes in gait useful for diagnostic and prognostic purposes.

Kinematics methods are an objective alternative, and are generally designed to measure linear and angular motion of various body parts during gait cycles using specialized targeted video camera technology. Kinetic methods employ various devices such as accelerometers, force platforms, etc., for determining the magnitude and timing of forces acting on various body parts during gait cycles. Implementing any one of the aforementioned gait analysis methods is a very complex and expensive undertaking, due in part to the complexity of the detection devices and the multifaceted signal detection and processing steps required.

An alternative method for assessing gait characteristics directly measures muscle function and is known as dynamic electromyography (EMG). EMG analysis utilizes a myoelectric signal that parallels the intensity of corresponding muscle activity, thus providing a useful indicator of the resulting mechanical effect. Determining and distinguishing the alterations in magnitude, phase, and duration of muscle action as associated with a particular gait pattern is very complex and computationally intensive.

An alternative type of gait detection device is a portable "footswitch" apparatus that is wearable on or within footwear, thus enabling collection of gait cycle data in a simpler, less expensive, and less restrictive manner than the previously described techniques. One such device is described in U.S. Pat. No. 6,360,597, issued to Hubbard. The gait analysis system disclosed by Hubbard comprises a force-detecting shoe insert enabling collection of gait interval data as the subject freely walks. While footswitch type devices, such as the portable gait analyzer disclosed by Hubbard, overcomes some of the aforementioned problems relating to the collection of gait pattern data, problems associated with the processing and analysis of collected gait data remain unresolved.

Since a wide variety of neuromuscular impairments manifest themselves to at least some extent in terms gait stability, an important analytic function is the determination of gait rhythmic patterns in terms of stride-to-stride fluctuations. Several methods are currently utilized to temporally analyze several dynamic aspects of gait. Power spectral analysis, such as Fourier spectral analysis has been a standard for temporal analysis of the dynamics of stride interval data presented as a time series. Autocorrelation decay is another such temporal spectral analysis technique often utilized in a complementary manner in conjunction with Fourier spectral analysis. The autocorrelation function estimates the extent to which a time series is self-correlated over different time lags, thus providing a measure of the system's "memory."

Processing the limited data points provided by a footswitch system using the foregoing gait analysis techniques is inadequate for detecting subtle alterations in gait patterns, and furthermore provides no means for associating a specified gait pattern with an underlying neuromuscular status. It can therefore be appreciated that a need exists for a system and method that efficiently collects gait data, quantifies the stability of gait from the collected data, and classifies the collected gait data in association with a neuromuscular status. The present invention addresses these as well as other needs unaddressed by prior art gait analysis devices and systems.

SUMMARY OF THE INVENTION

A method, system, and article of manufacture for detecting, recording, quantifying, and classifying gait data are disclosed herein. In one embodiment, the method of the invention includes a step of detecting foot contact events using a portable sensor device. Stride data is collected by processing the detected foot contact events to obtain and record gait pattern data. At least one gait stability value is determined from the gait pattern data using a specified gait stability metric. The gait stability value is preferably a mathematical chaos value which is processed utilizing a clustering correlation algorithm to classify the gait pattern data in association with a neuromuscular status. In a preferred embodiment, fuzzy logic is utilized to correlate the determined gait stability value with a plurality of gait stability values each associated with a distinct neuromuscular status.

The above as well as additional objects, features, and advantages of the present invention will become apparent in the following detailed written description.

BRIEF DESCRIPTION OF THE DRAWINGS

The novel features believed characteristic of the invention are set forth in the appended claims. The invention itself however, as well as a preferred mode of use, further objects and advantages thereof, will best be understood by reference to the following detailed description of an illustrative embodiment when read in conjunction with the accompanying drawings, wherein:

DETAILED DESCRIPTION OF ILLUSTRATIVE EMBODIMENT(S)

The present invention is generally directed to a biomedical device and method that provide an accurate and efficiently obtained assessment of neuromuscular health from the pattern of a subject's gait. While the preferred embodiments described herein are directed to detection and processing of human gait patterns, it will be understood by those skilled in the art that the same structural and procedural principles may be applicable in a veterinary context, i.e., to the gait patterns of animals including non-bipedal animals, such as horses, dogs, etc.

As explained in further detail below with reference to the figures, the gait analysis system of the present invention may generally comprise a gait data collection device and a gait data processing system. The gait data collection device hardware may include force-sensitive sensors, such as strain gauge sensors that are strategically positioned in the subject's footwear. These force sensing sensors may be deployed on shoes insoles that fit into the subject's shoe. The sensors detect gait-related events such as the initiation and termination of the foot contact times during gait. The detected gait events are amplified, filtered, and smoothed by a small external circuit and stored as binary data in a portable data collection device that is preferably worn by the subject. The portable nature of the gait data collection device eliminates the need for tethering or otherwise restricting the range of motion of the subject, thereby maximizing simulation of the subject's "natural" gait and enhancing accuracy of the results. In this manner, for example, the system may be used to collect data while the subject is walking/running in his/her familiar environment rather than being limited to an unfamiliar clinical environment.

After collecting the foot contact information for the gait pattern, the sensor data is seamlessly downloaded to a data processing system, such as a personal computer via a suitable communication connection such as a serial bus channel. As explained in further detail below with reference to FIGS. 3-6, the collected gait pattern data are processed to determine at least one gait stability value using a specified gait stability metric. In a preferred embodiment, the gait stability metric is a chaos metric. The chaos metric data is processed utilizing fuzzy logic to classify the gait pattern in association with a neuromuscular status. In this manner, a clinician is provided with a highly accurate assessment of gait stability that is maximally leveraged using a fuzzy clustering algorithm to derive optimal diagnostic and/or prognostic indicia from limited gait pattern data.

Figure 1:
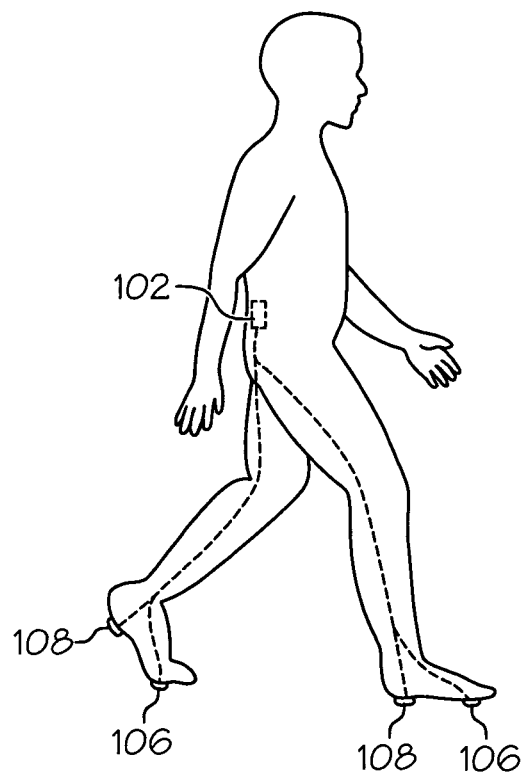
FIG. 1 depicts a portable gait monitor device as worn by a subject in accordance with the present invention.
Figure 2:
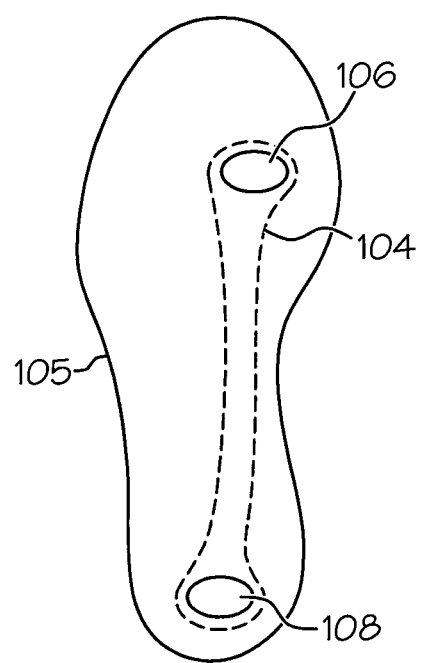
FIG. 2 illustrates the positioning of force sensitive resistor sensors on the insole worn by a subject in accordance with the present invention.

With reference now to the figures, wherein like reference numerals refer to like and corresponding parts throughout, and in particular with reference to FIGS. 1 and 2, there is depicted a portable gait monitor device as worn by a subject in accordance with the present invention. The illustrated gait monitor device generally comprises a portable monitor unit 102 wearable by a human or animal subject. As shown in the depicted embodiment, portable monitor 102 is preferably attached at approximately the waist of the subject to minimize interference with the natural gait of the subject in terms of leg and arm movement.

As further shown in FIGS. 1 and 2, the gait monitor device further includes a sensor assembly 104 that provides the sensory interface for detecting foot contact events. In a preferred embodiment, sensor assembly 104 includes at least a forefoot, or "toe off" sensor 106 and a heel strike (HS) sensor 108 for providing data about the initiation and termination of foot contact times during each gait cycle. TO sensor 106 and HS sensor 108 are preferably positioned on the surface of one or both insoles 105 fitted in the footwear of the subject such that TO sensor 106 is approximately centered under the front forefoot proximate the portion of the front ball of the foot longitudinally aligned with the subject's big toe. HS sensor 108 is preferably centered below the approximate center of the subject's heel.

In a preferred embodiment, TO sensor 106 and HS sensor 108 are force sensing resistors that are disposed on the subject-specific insoles 105, which are preferably constructed of a polyurethane material. TO sensor 106 and HS sensor 108 are specialized transducers, outputting analog signals (typically voltage levels) having a specified range corresponding to the load applied at any given time. In one embodiment, for example, sensors 106 and 108 output analog voltage levels ranging from 0 V, corresponding to a specified minimum load, to 3.2 V, corresponding to a specified maximum load. Among the foot contact event metrics that may be detected by TO sensor 106 in conjunction with HS sensor 108 are absolute and relative HS and TO timing. In addition, and importantly in many gait analysis procedures associated with neuromuscular diagnosis, the stance phase duration between each heel strike and toe-off is also cooperatively detected by TO sensor 106 and HS sensor 108.

As further depicted in FIG. 1, sensor assembly 104 is electronically or otherwise communicatively coupled to portable monitor device 102, which receives, conditions and collects the gait pattern data as described in further detail with reference to FIG. 3.

The use of the gait monitor device shown in FIGS. 1 and 2 is substantially simpler, less expensive, less restrictive and less invasive of a subject than traditional gait data collection systems that employ multiple high-speed cameras, force platforms, and electromyography. As now described with reference to FIGS. 3-6, the present invention further includes electronic and program product processing interfaces and modules that optimally characterize and classify gait pattern stability from the gait data collected from the device shown in FIGS. 1 and 2 or other gait pattern collection systems. In this aspect, the present invention includes a gait data processing system which, as explained below with reference to the figures, may be one of several possible combinations of hardware, firmware, and software devices and modules. Referring to FIG. 3, there is illustrated a high-level block diagram depicting a gait collection and processing system 300 in accordance with a preferred embodiment of the present invention. As shown in FIG. 3, system 300 generally comprises sensor assembly 104 communicatively coupled, such as by cable or local wireless technology, to portable monitor 102. As previously depicted with reference to FIG. 1, portable monitor 102 and sensor assembly 104 together form a subject-wearable apparatus that enables the collection of gait pattern data over extended times and distances, and in a manner that minimally interferes with the subject's "natural" gait.

Figure 3:
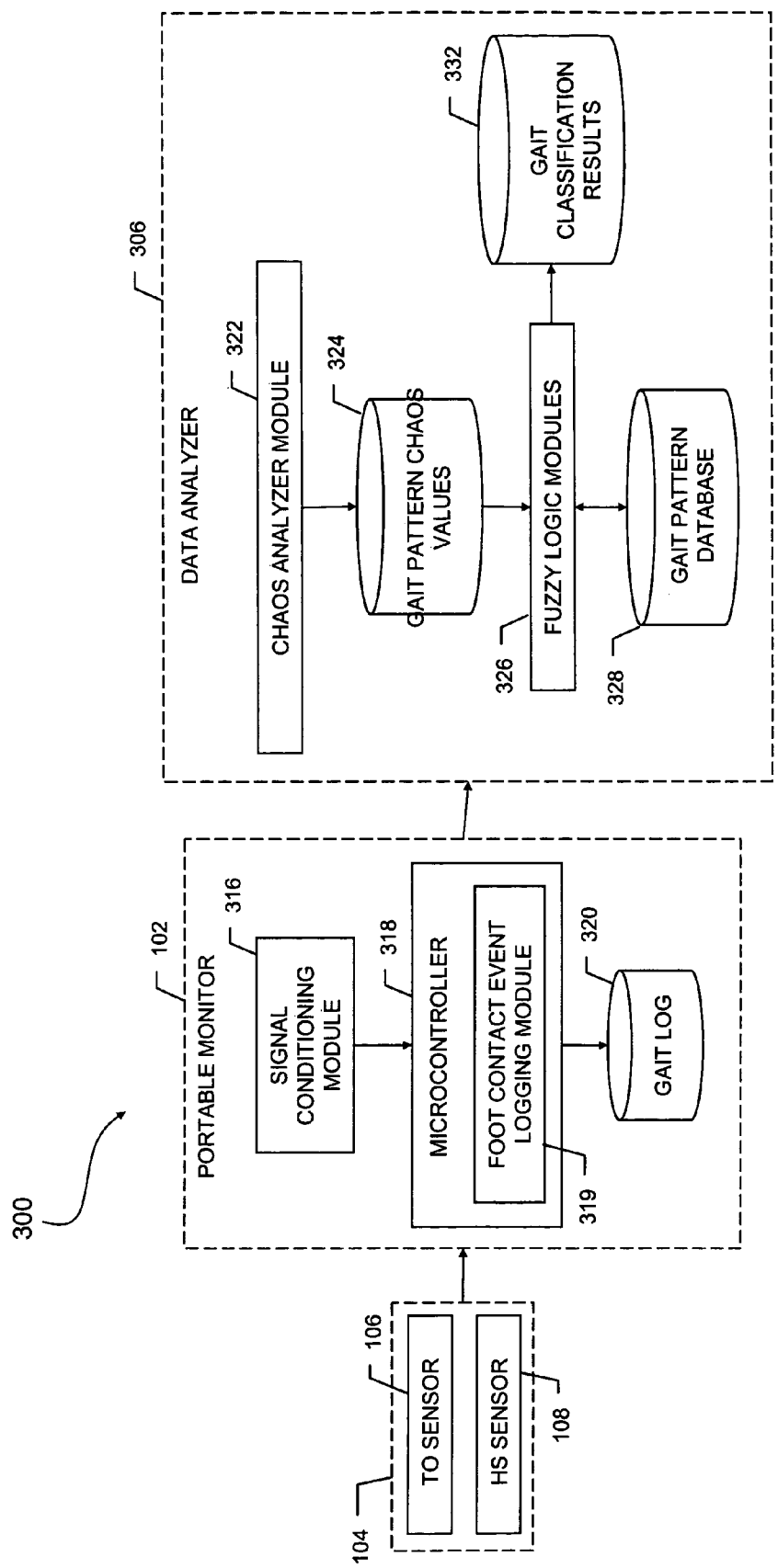
FIG. 3 is a high-level block diagram depicting a gait collection and processing system in accordance with a preferred embodiment of the present invention.

As further depicted in FIG. 3, portable monitor 102 includes various components and modules including a signal conditioning module 316 that receives and conditions the foot contact event signals from the sensor assemblies 104 attached to the insoles of one or more of the subject's feet. Signal conditioning module 316 generally includes circuit and/or program modules and devices for improving the resolution, or readability, of the possibly noisy analog signals received at a specified sampling rate from sensor assembly 104. Assuming the received sensor signals are analog, signal conditioning module 316 includes an analog-to-digital converter (not depicted). Other features not depicted, but possibly included within signal conditioning module 316, include signal amplifiers and filters.

Portable monitor 102 further includes data collection and processing features including a microcontroller 318 and gait log storage 320. Microcontroller 318 may be one of many possible microcontroller variations and fundamentally comprises processing/instruction and memory features (not depicted). Microcontroller 318 may include hardware-based instruction means that receive and process the conditioned and digitized foot contact event data from signal conditioning module 316. Microcontroller 318 preferably includes instructions for storing the data in an organized manner within gait log storage 320, such as a logged data series having specified file system designators such as a file or directory names. Specifically, microcontroller 318 includes a foot contact event logging module 319 that detects and processes foot contact signals generated by the respective TO and HS sensors 106 and 108. In one embodiment, foot contact event logging module 319 includes instructions for temporally measuring each individual stride interval by detecting and logging the period between consecutive heel strike signals for the same foot from the HS sensor 108 for one or both feet. While stride time interval is generally the fundamental gait pattern indicator that can be used in gait stability analysis, the processing and program means within microcontroller 318 may further include instructions which, in combination with additional locomotive pattern parameters such as distance traveled, may be used to measure other gait indicia including stride distance, velocity, foot support patterns, etc.

Gait collection and processing system 300 further comprises a data analyzer 306 that may be communicatively coupled to portable monitor 102, such as when the gait pattern data for a given subject is to be analytically processed. As explained above, the apparatus comprising sensor assembly 104 and portable monitor 102 is preferably a non-tethered design. Therefore, and in a preferred embodiment, after gait pattern data has been detected and collected by portable monitor 102, an electronic or wireless connectivity medium and protocol, such as the connectively specified by the universal serial bus (USB) wire or wireless standard may be utilized to couple portable monitor 102 to data analyzer 306.

Data analyzer 306 includes electronic devices and interfaces as well as program modules for quantifying and classifying the stride data and/or other gait pattern metrics collected by the wearable apparatus shown in FIGS. 1, 2, and 3. In one aspect, the processing performed by data analyzer 306 reveals various gait rhythm characteristics which would otherwise remain opaque to conventional temporal spectral processing such as Fourier spectral processing. To this end, and in the preferred embodiment depicted in FIG. 3, data analyzer 306 generally comprises a chaos analyzer module 322 that determines one or more gait stability values of at least one gait stability metric from a set of gait pattern data obtained or otherwise received from portable monitor 102. In a preferred embodiment, chaos analyzer 322 includes electronic and/or program modules that determine values for one or more chaotic properties such as the Lyapunov exponent and correlation dimension of a time series gait pattern received from portable monitor 102. As utilized herein, "chaos," "chaos metrics," "chaotic properties," and similar terms refer to non-periodic, seemingly random behavior in a deterministic system that exhibits sensitive dependence on initial conditions. "Chaos analysis," refers to methods and techniques utilized in various mathematics and physics contexts that quantifies the behavior of non-linear dynamical systems that exhibit the aforementioned phenomena known as chaos.

As is known in the art of chaos analysis techniques, a Lyapunov exponent is generally a measure of the exponential divergence of a system and provides a quantification of the rate of divergence of a system exhibiting chaos. As such, Lyapunov exponents reveals the sensitivity of a system to deviate from a static and periodical regimen from a particular starting point. Another chaos metric that may be utilized as a gait stability metric is known in the field of chaos theory analysis as the correlation dimension. As known in the field of chaos analysis, the correlation dimension is a measure of how many data points of a dynamic system are organized in state space. The correlation dimension describes the fractal area that an attractor occupies and provides a measure of the system complexity.

Chaos analyzer 322 is preferably deployed as a graphical user interface accessible program executed on a data processing system such as that described below with reference to FIG. 4. Chaos analyzer 322 processes the gait pattern data received from gait log 320 to quantify the level of chaos exhibited by the gait data in question. In one embodiment, chaos analyzer 322 generates values 324 for the Lyapunov exponent and correlation dimension from the time series gait pattern data within gait log 320. The gait pattern chaos values 324 determined by chaos analyzer 322 may be stored in a data storage device such as memory or disk storage.

Data analyzer 306 further comprises a set of one or more fuzzy logic modules 326 that are utilized to process the stability metric(s) determined by chaos analyzer 322 in association with a given gait pattern. Specifically, fuzzy logic modules 326 comprise one or more modules that perform fuzzy logic clustering among the determined chaos metric data 324 and one or more pre-specified chaos metrics 328 that are each associated with a neuromuscular status. Such status-associated chaos metrics 328 may be stored in a memory or other data storage device. The clustering correlation performed by fuzzy logic modules 326 results in the classification of the subject gait pattern in accordance with the patterns to which it is compared and the classification results may be stored in a gait classification results storage 332.

Figure 4:
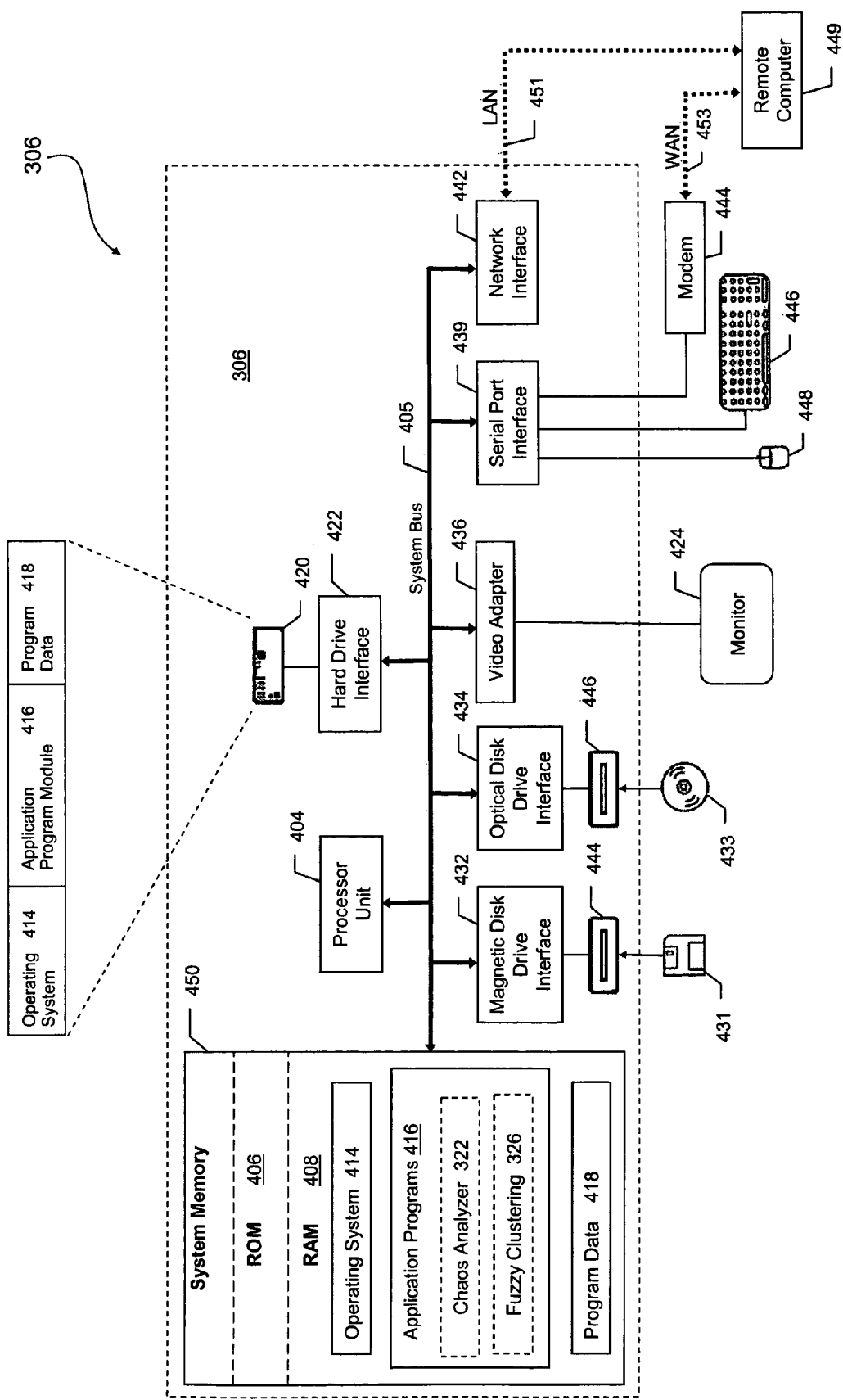
FIG. 4 illustrates a data processing system adapted for processing collected gait data in accordance with the present invention.

With reference to FIG. 4, data analyzer 306 is depicted as a data processing system adapted for processing collected gait data in accordance with the present invention. For discussion purposes, the data processing system is described as a personal computer, such as a desktop or portable computer. However, as used herein, the terms "data processing system," "computer," and the like, are intended to mean essentially any type of computing device or machine that is capable of running a software product.

While various aspects of the invention are described in FIG. 4 and elsewhere in the general context of programs running on an operating system in conjunction with a personal computer, those skilled in the art will recognize that the invention may also be implemented in combination with other program modules. Generally, program modules include routines, programs, components, data structures, etc. that perform particular tasks or implement particular abstract data types. Moreover, those skilled in the art will appreciate that the invention may be practiced with other computer system configurations, including multiprocessor systems, microprocessor-based or programmable consumer electronics, mini-computers, mainframe computers, and the like.

As shown in FIG. 4, data analyzer 306 generally comprises a computer 415, having a processing unit 404, a system memory 450, and a system bus 405 that couples system memory 450 to processing unit 404. The system memory 450 includes read only memory (ROM) 406 and random access memory (RAM) 408. Computer 415 further includes a hard disk drive 420, a magnetic disk drive 444, e.g., to read from or write to a removable disk 431, and an optical disk drive 446, e.g., for reading a CD-ROM disk 433 or to read from or write to other optical media. Hard disk drive 420, magnetic disk drive 444, and optical disk drive 446 are connected to system bus 405 by a hard disk drive interface 422, a magnetic disk drive interface 432, and an optical drive interface 434, respectively. The drives and their associated computer-readable media provide non-volatile storage for computer 415.

A number of program modules may be stored in the drives and system memory 450, including an operating system 414, application program modules 416, and program data 418. In accordance with the depicted embodiment, a set of one or more chaos analyzer modules 322 and fuzzy cluster modules 326 are included as applications within system memory 450. As explained in further detail below with reference to FIGS. 5 and 6 chaos analyzer modules 322 and fuzzy cluster modules 326 cooperatively provide a clinician a rapid diagnostic/prognostic assessment for a given gait pattern in association with a neuromuscular status.

A user may enter commands and information into computer 415 through a keyboard 446 and pointing device, such as a mouse 448. Other input devices (not shown) may include a microphone, joystick, game pad, satellite dish, scanner, or the like. These and other input devices are often connected to processing unit 404 through a serial port interface 439 that is coupled to the system bus, but may be connected by other interfaces, such as a universal serial bus. A monitor 424 or other type of display device is also connected to system bus 405 via an interface, such as a video adapter 436.

Computer 415 may operate in a networked environment using logical connections to one or more remote computers, such as a remote computer 449. The remote computer 449 may be a server, a router, a peer device or other common network node, and typically includes many or all of the elements described relative to computer 415. The logical network connections depicted in FIG. 4 include a local area network (LAN) 451 and a wide area network (WAN) 453. Such networking environments are commonplace in offices, enterprise-wide computer networks, Intranets and the Internet.

When used in a LAN networking environment, computer 415 is connected to LAN 451 through a network interface 442. When used in a WAN networking environment, computer 415 typically includes a modem 444 or other means for establishing communications over WAN 453, such as the Internet. The modem 444, which may be internal or external, is connected to system bus 405 via serial port interface 439. In a networked environment, program modules depicted relative to computer 415, or portions thereof, may be stored in one or more remote (i.e., network distributed) memory storage devices. It will be appreciated that the network connections shown are exemplary and other means of establishing a communications link between the computers may be used.

Figure 5:
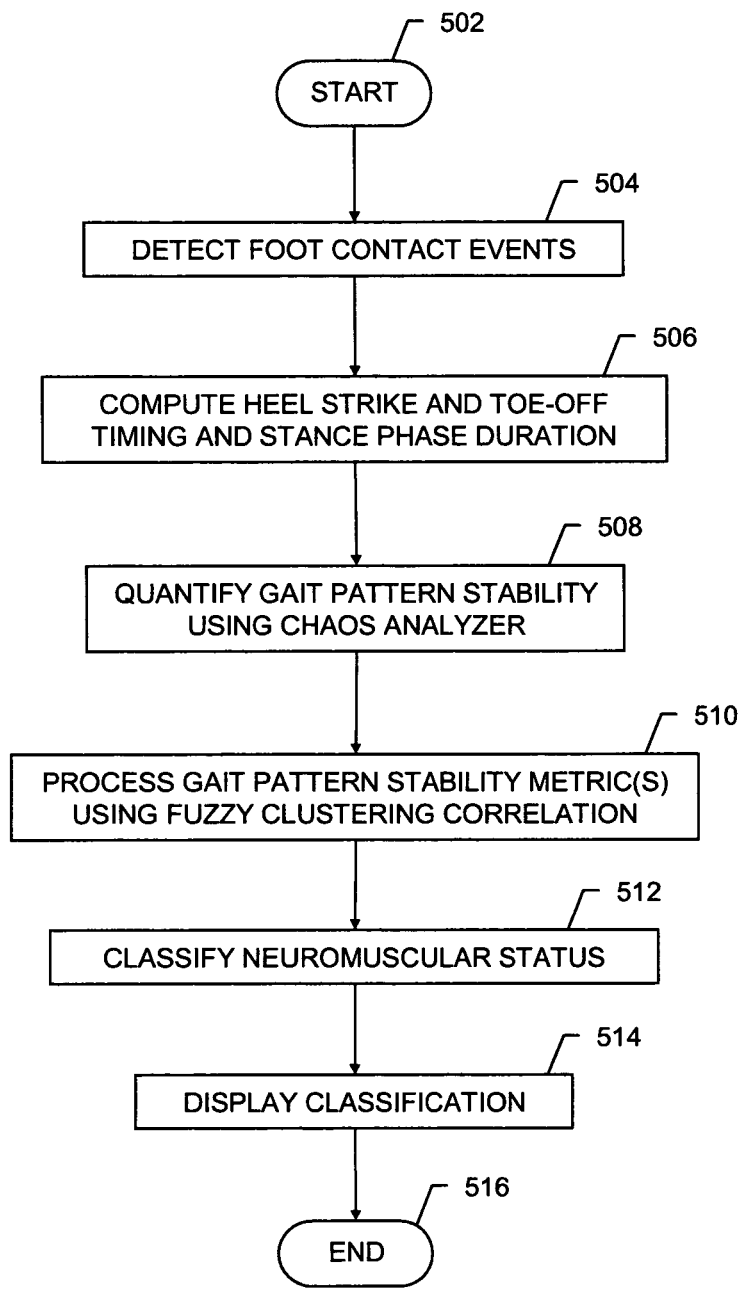
FIG. 5 is a high-level flow diagram depicting steps performed during collection and processing of gait data in accordance with the present invention.

FIG. 5 is a high-level flow diagram depicting steps performed during collection and processing of gait data in accordance with the present invention. The process begins as shown at steps 502 and 504 with the sensor assembly 104 depicted in FIGS. 1, 2, and 3 being utilized to detect one or more foot contact events during a given test interval over which the subject walks and/or runs over multiple strides or over a specified time period. Depending on the particular design of sensor assembly 104 and the correspondingly programmed event logging modules within microcontroller 318, various gait pattern metrics may be utilized to quantify gait data from the foot contact events. For example, and as depicted at step 506, the heel strike and toe-off timing and stance phase duration (i.e. period between a given heel strike and corresponding toe-off) may be computed from data detected at step 504.

Proceeding as illustrated at step 508, chaos analyzer 322 is utilized to quantify the stability of the collected gait pattern data. In a preferred embodiment, chaos analyzer 322 includes instructions and processing routines that determine at least one gait stability value from the gait pattern data using a specified gait stability metric. More particularly, and in a preferred embodiment, chaos analyzer 322 determines one or more chaos values in association with the gait pattern data. Next, as illustrated at step 510, the chaos value(s) determined at step 508 are utilized to determine the level of association of the subject gait pattern with one or more pre-classified sets of gait pattern data. Specifically, the determined chaos value(s) 324 and pre-classified chaos values 328, the latter having a specified association with neuromuscular conditions, are input to fuzzy logic module 326. Fuzzy logic module 326 processes chaos value(s) 324 in association with the pre-classified values 328 preferably using fuzzy logic clustering algorithms such as fuzzy subtractive clustering and/or fuzzy c-means clustering. As a result of the fuzzy logic cluster performed at step 510, the subject gait pattern data 320 is classified as having a relative correlation to the pre-classified values 328 as shown at step 512. In a preferred embodiment, the classification determined in accordance with the fuzzy logic clustering is displayed on a user display (step 514) and the process terminates (step 516).

The use of clustering correlation to process and ultimately classify gait pattern chaos values provides a highly accurate diagnostic/prognostic tool that is relatively simple and inexpensive to implement and provides clinicians with a variety of analytic options. This method may be advantageously applied in degenerative and regenerative contexts such as for neuromuscular disorders or rehabilitation evaluation. As a prognostic tool, for example, the pre-classified gait pattern data 328 may include multiple sets of data reflecting various levels of Parkinson's chaotic dynamics. The fuzzy clustering modules 326 may utilize a fuzzy logic clustering technique such as fuzzy subtractive clustering and/or fuzzy c-means clustering to determine a relative association between the subject's gait pattern and one or more of the benchmark sets.

Figure 6:
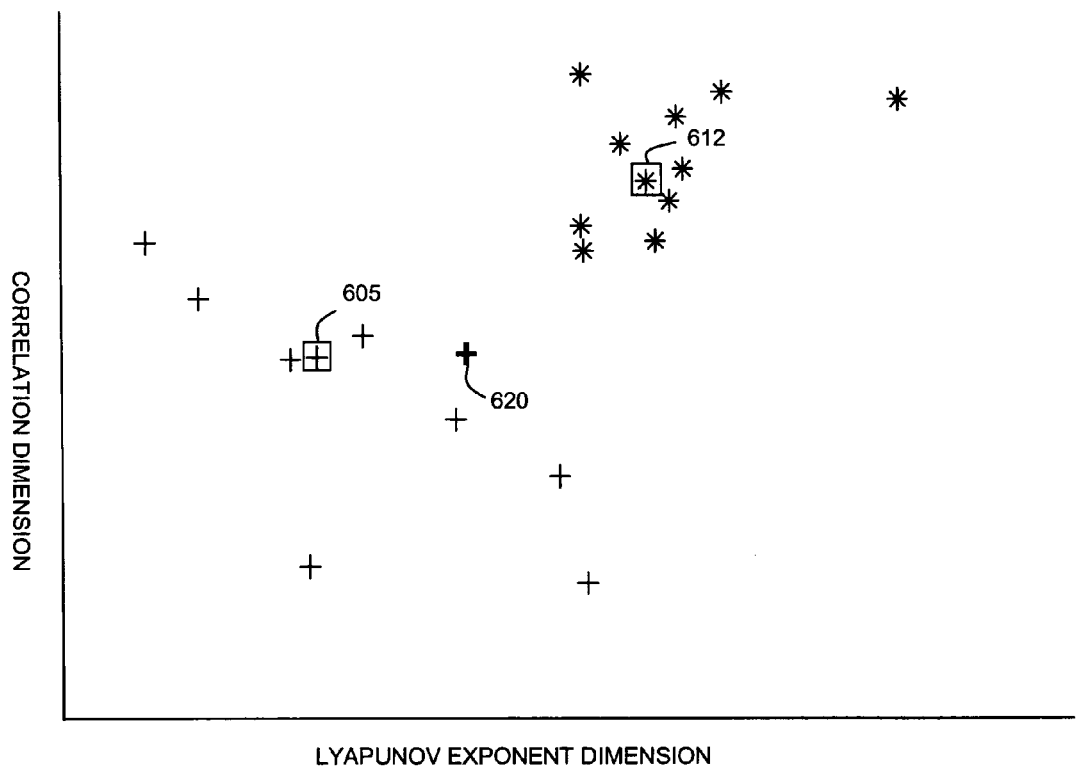
FIG. 6 illustrates a graphical representation of an exemplary fuzzy logic classification rendered in accordance with the present invention.

FIG. 6 illustrates a graphical representation of an exemplary cluster data correlation rendered for classification of a subject gait pattern relative to normal and abnormal gait patterns in accordance with the present invention. As shown in the depicted embodiment, the two-dimensional graphical representation is defined in Cartesian axes representing a correlation dimension and Lyapunov exponent dimension. In one embodiment, the correlation dimension and Lyapunov exponent dimension represented in the graph may represent quantified values of gait stability as reflected by the correlation dimension and Lyapunov exponent.

Some of the data points, represented in the depicted embodiment by +signs, represent a set of gait stability metrics that have a pre-determined association with a level of gait pathology. The other data points, represented in the depicted embodiment by * signs, represent a set of gait stability metrics that have a pre-determined association with various healthy gaits.

The data points reflecting various levels of pathology (represented by +'s) and health (represented by *'s) are distributed within the within the space in accordance with a clustering correlation algorithm that processes gait stability metrics obtained from known pathological and healthy gait patterns with each of the data points representing a given gait pattern. In a preferred embodiment, the data processed by the fuzzy logic algorithm are chaos values quantified as Lyapunov exponents, correlation dimensions, etc., that have been computed or otherwise derived as described in the foregoing description. The fuzzy logic algorithm preferably implements a fuzzy logic clustering technique, such as fuzzy subtractive clustering or fuzzy c-means clustering, to generate the data point distribution which graphically displays the relative correlation between data points representing different gait patterns. In a preferred embodiment, the gait patterns corresponding to the pathological and healthy sets are recorded in gait pattern database 328.

Classification of a neuromuscular status (depicted at step 512 of FIG. 5) is further illustrated in FIG. 6 with respect to the healthy and pathological data sets. Data points 605 and 612, respectively, represent the cluster center for the pathological and healthy data sets. As part of the classification step, the fuzzy logic clustering technique further generates a data point 620 that corresponds to the subject gait pattern quantified as illustrated at step 508 of FIG. 5. The graphical representation and distribution of point 620 with respect to the multiple pre-classified data points provides a relative classification of the gait pattern represented by point 620.

In the foregoing manner, the gait analysis system and method of the present invention provides a succinct quantification of gait stability in a multi-dimensional state space that contains the range of values for the characteristics of a given gait pattern. The use of fuzzy clustering techniques to classify a given gait pattern state space quantification provides a sensitive and accurate diagnostic/prognostic tool with limited input gait pattern data.

While the invention has been particularly shown and described with reference to a preferred embodiment, it will be understood by those skilled in the art that various changes in form and detail may be made therein without departing from the spirit and scope of the invention. These alternate implementations all fall within the scope of the invention.

What is claimed is:

1. A method for analyzing gait comprising:
    collecting gait pattern data via a gait monitor device having a portable monitor unit adapted to be wearable by a subject and a gait data collection device including at least one toe-off (TO) force-sensitive sensor adapted to be positioned on a surface of an insole near a front ball of a foot of the subject, and at least one heel strike (HS) force-sensitive sensor adapted to be positioned on a surface of the insole below a heel of the subject, the gait data collection device communicatively coupled to the portable monitor unit and adapted to provide data to the portable monitor unit about initiation and termination of foot contact times during a gait cycle;
    specifying, via a data analyzer communicatively coupled to the portable monitor unit, a gait stability metric that is used to quantify a stability associated with the collected gait pattern data;
    determining, via one or more processors of the data analyzer, a gait stability value from the gait pattern data using the specified gait stability metric;
    wherein the determined gait stability value is a quantification of the stability associated with the collected gait pattern data;
    processing, via one or more processors of the data analyzer, the determined gait stability value in association with a pre-classified gait stability value utilizing a clustering correlation module of a memory of the data analyzer to determine the level of association of the collected gait pattern data with pre-classified gait pattern data,
    wherein the pre-classified gait pattern data has a pre-specified association with a neuromuscular status; and
    classifying, via one or more processors of the data analyzer, the gait pattern data in association with the neuromuscular status based on the determined level of association of the collected gait pattern data with pre-classified gait pattern data.

2. The method of claim 1, wherein the collecting gait pattern data further comprises:
    collecting the gait pattern data by detecting and recording foot contact events.

3. The method of claim 2, said collecting further comprising:
    collecting data related to foot contact events to detect gait-related events including one or more of (a) initiation and termination of foot contact times during gait, (b) a stance phase duration between heel strike and toe-off, (c) absolute and relative heal strike and toe-off timing; (d) stride distance; (e) velocity; and (f) foot support patterns; and
    processing, via one or more processors of the data analyzer, the recorded foot contact events to obtain one or more gait stability values using the gait stability metric and at least one stride interval data.

4. The method of claim 1, wherein:
    said gait stability metric is one of multiple gait stability metrics,
    said specified gait stability metric is a chaos metric and chaos metric data is processed, via one or more processors, to classify the gait pattern in association with a neuromuscular status and said stability is provided by one of multiple measures for stability which measures include: (a) a rate of divergence; (b) a complexity measure, and (c) other measures for stability.

5. The method of claim 4, wherein the chaos metric is included among the group including (a) Lyapunov exponent and (b) a correlation dimension.

6. The method of claim of claim 4, wherein processing, via one or more processors, the gait stability value comprises using a fuzzy logic clustering technique to correlate the gait stability value with a plurality of other gait stability values each associated with a distinct neuromuscular status, wherein a fuzzy clustering algorithm leverages a determined gait stability value to derive one or more of optimal diagnostic indicia and prognostic indicia from the gait pattern data.

7. The method of claim 6, wherein the fuzzy logic clustering technique is included in the group comprising fuzzy subtractive clustering and fuzzy c-means clustering.

8. A system for analyzing gait comprising:
    a portable monitor unit adapted to be wearable by a subject;
    a gait data collection device communicatively coupled to the portable monitor unit and adapted to provide data to the portable monitor unit about initiation and termination of foot contact times during a gait cycle, the gait data collection device including at least one toe-off (TO) sensor adapted to be positioned on a surface of an insole near a front ball of a foot of the subject, and at least one heel strike (HS) sensor adapted to be positioned on a surface of the insole below a heel of the subject; and
    a data analyzer communicatively coupled to the portable monitor unit and having at least one processing unit and a memory, wherein a gait stability value from gait pattern data using a specified gait stability metric is determined and
used to quantify a stability associated with the collected gait pattern data; and
wherein the determined gait stability value is processed in association with a pre-classified gait stability value utilizing clustering correlation to determine the level of association of the collected gait pattern data with pre-classified gait pattern data, the pre-classified gait pattern data having a pre-specified association with a neuromuscular status; and the gait pattern data is classified in association with the neuromuscular status based on the determined level of association of the collected gait pattern data with pre-classified gait pattern data.

9. The system of claim 8, further comprising.
wherein said data analyzer completes the functions of:
collecting data related to foot contact events to detect gait-related events, including one or more of (a) initiation and termination of foot contact times during gait, (b) a stance phase duration between heel strike and toe-off, (c) absolute and relative heal strike and toe-off timing; (d) stride distance; (e) velocity; and (f) foot support patterns; and
processing the recorded foot contact events to obtain one or more gait stability values using the gait stability metric and at least one stride interval data.

10. The system of claim 8, wherein said specified gait stability metric is a chaos metric, and chaos metric data is processed to classify the gait pattern in association with a neuromuscular status and wherein said stability is provided by one of multiple measures for stability which measures include: (a) a rate of divergence; (b) a complexity measure; and (c) other measures for stability.

11. The system of claim 10, wherein the chaos metric is included among the group including (a) Lyapunov exponent and (b) a correlation dimension.

12. The system of claim of claim 10, wherein said data analyzer utilizes a fuzzy logic clustering technique to correlate the gait stability value with a plurality of gait stability values each associated with a distinct neuromuscular status, wherein a fuzzy clustering algorithm leverages a determined gait stability value to derive one or more of optimal diagnostic indicia and prognostic indicia from the gait pattern data.

13. The system of claim 12, wherein the fuzzy logic clustering technique is included in the group comprising fuzzy subtractive clustering and fuzzy c-means clustering.

14. A system comprising a processor, a computer-readable storage medium having encoding thereon computer-executable instructions for analyzing gait, said computer-executable instructions executable by the processor to:
collect gait pattern data via a gate monitor device having a portable monitor unit adapted to be wearable by a subject and a gait data collection device, the gait data collection device including at least one force-sensitive sensor adapted to be positioned on a surface of an insole;
specify a gait stability metric that is used to quantify a stability associated with the collected gait pattern data;
determine a gait stability value from the gait pattern data using the specified gait stability metric;
wherein the determined gait stability value is a quantification of the stability associated with the collected gait pattern data;
process the determined gait stability value in association with and a pre-classified gait stability value utilizing clustering correlation to determine the level of association of the collected gait pattern data with pre-classified gait pattern data,
wherein the pre-classified gait pattern data has a pre-specified association with a neuromuscular status; and
classify the gait pattern data in association with the neuromuscular status based on the determined level of association of the collected gait pattern data with pre-classified gait pattern data.

15. The system of claim 14, wherein wherein said computer-executable instructions are executable by the processor to collect the gait pattern data by detecting and recording foot contact events.

16. The system of claim 15, said wherein said computer-executable instructions are executable by the processor to further:
collect data related to foot contact events to detect gait-related events, including one or more of (a) initiation and termination of foot contact times during gait, (b) a stance phase duration between heel strike and toe-off, (c) absolute and relative heal strike and toe-off timing; (d) stride distance; (e) velocity; and (f) foot support patterns; and
process the recorded foot contact events to obtain one or more gait stability values using the gait stability metric and at least one stride interval data.

17. The system of claim 14, wherein:
said gait stability metric is one of multiple gait stability metrics;
said specified gait stability metric is a chaos metric, and chaos metric data is processed to classify the gait pattern in association with a neuromuscular status and
said stability is provided by one of multiple measures for stability which measures include: (a) a rate of divergence; (b) a complexity measure; and (c) other measures for stability.

18. The system of claim 17, wherein the chaos metric is included among the group including (a) Lyapunov exponent and (b) a correlation dimension.

19. The system of claim of claim 18, wherein to process the gait stability value comprises using a fuzzy logic clustering technique to correlate the gait stability value with a plurality of pre-classified gait stability values, each associated with a distinct neuromuscular status, wherein a fuzzy clustering algorithm leverages a determined gait stability value to derive one or more of optimal diagnostic indicia and prognostic indicia from the gait pattern data.

20. The system of claim 19, wherein the fuzzy logic clustering technique is included in the group comprising fuzzy subtractive clustering and fuzzy c-means clustering.

* * * * *